United States Patent [19]

Williams, Jr. et al.

[11] 4,196,425
[45] Apr. 1, 1980

[54] PATIENT ACTIVITY MONITORING SYSTEM

[75] Inventors: Clyde E. Williams, Jr., P.O. Box 527, Rancho Santa Fe, Calif. 92067; David S. Weekly, Encinitas, Calif.

[73] Assignee: by said David S. Weekly said Clyde E. Williams, Rancho Santa Fe, Calif.

[21] Appl. No.: 923,220

[22] Filed: Jul. 10, 1978

[51] Int. Cl.² .............................................. G08B 21/00
[52] U.S. Cl. ................................. 340/573; 340/556; 340/600
[58] Field of Search .............. 340/573, 556, 600, 538; 128/2 S, 2 A, 664, 665

[56] References Cited
U.S. PATENT DOCUMENTS

| Re. 28,754 | 3/1976 | Cook et al. | 340/573 |
|---|---|---|---|
| 3,573,817 | 4/1971 | Akers | |
| 3,633,199 | 1/1972 | Curry et al. | 340/538 |
| 3,704,461 | 11/1972 | Rose et al. | 340/556 |
| 3,752,978 | 8/1973 | Kahl, Jr. et al. | 340/555 |
| 3,796,208 | 3/1974 | Bloice | 128/2 A |
| 3,816,745 | 6/1974 | Primm et al. | 340/556 |
| 3,831,586 | 8/1974 | Petit | 340/573 |
| 3,842,403 | 10/1974 | Konopka | |
| 3,914,753 | 10/1975 | Cho | 340/556 |
| 3,924,253 | 12/1975 | Marino | 340/556 |
| 3,946,241 | 3/1976 | Malinowski | |
| 3,988,726 | 10/1976 | Reiss et al. | |
| 3,991,414 | 11/1976 | Moran | 340/573 |
| 3,991,746 | 11/1976 | Hanna | 128/2 S |
| 4,148,020 | 4/1979 | Siemer et al. | 340/538 |

Primary Examiner—Glen R. Swann, III
Attorney, Agent, or Firm—Fischer and Tachner

[57] ABSTRACT

In order to monitor the movements of a patient who is confined to a bed and to alert supervisory personnel in the event that the patient attempts an unauthorized departure therefrom, an array of radiant energy emitters and a corresponding array of radiant energy detectors are installed in the headboard and in the footboard of the bed. In one embodiment, emitters supply infrared energy to the detectors so as to cover the bed with a blanket of invisible light. When the transmission of infrared energy is interrupted for a predetermined time by an overactive patient, both local and remote warning signals are generated to immediately alert the supervisory personnel to the possibility of impending patient injury.

28 Claims, 7 Drawing Figures

PATIENT ACTIVITY MONITORING SYSTEM

BACKGROUND OF THE INVENTION

This invention relates to a patient activity monitoring system to monitor the movements of a patient who is confined to a bed and to alert supervisory personnel in the event that the patient attempts any unauthorized excessive activity or departure therefrom.

Many serious injuries are known to occur each year in hospitals and nursing homes to certain overactive, bed confined patients, who, without proper authorization, attempt to leave their bed by climbing over the side restraining rails or footboard of the bed. For example, a bed confined patient may be either sedated, mentally incapacitated, or may have sustained serious bodily injury that requires complete immobilization for proper recovery. In the past, supervisory personnel have been stationed in the overactive patient's room to prevent the patient from attempting any unauthorized movements which might lead to an accidental fall and serious injury. However, this procedure has proven both time consuming and expensive.

Therefore, the prior art has included various signaling apparatus which alerts the supervisory personnel in the event of unauthorized patient moements. By way of example, some of the prior art signaling apparatus includes pressure sensitive devices positioned under the bed mattress and various capacitance devices, the capacitance of which changes with the movements of a patient. The following U.S. patents are indicative of some of the aforementioned prior art signaling apparatus: Nos.

| | |
|---|---|
| 3,573,817 | Apr. 6, 1971 |
| 3,991,414 | Nov. 9, 1976 |
| 3,991,746 | Nov. 16, 1976 |
| Re.28,754 | Mar. 30, 1976 |

However, these prior art signaling techniques are ineffective, inasmuch as a relatively long time delay is required before an unsafe patient condition can be sensed and a warning signal transmitted to the appropriate supervisory personnel. Therefore, by the time that the supervisory personnel can either receive or respond to the warning signal, an overactive patient may have already incurred serious injury as the result of a fall or the like.

The U.S. patents below are examples of optical systems comprised of emitters, which transmit a beam of radiation, and detectors, which sense any interruption of the beam, to thereby provide an indication of intrusion into a monitored zone: Nos.

| | |
|---|---|
| 3,752,978 | Aug. 14, 1973 |
| 3,842,403 | Oct. 15, 1974 |
| 3,946,241 | Mar. 23, 1976 |
| 3,988,726 | Oct. 26, 1976 |

However, none of these optical systems are adapted to interface with a bed to accurately detect unauthorized and excessive movements of a bed confined patient. More particularly, none of the aforementioned patents shows or discloses an optical system which would distinguish inadvertent or random patient movements from an intentional patient attempt to depart from his bed. Hence, numerous false alarms would be commonplace. What is more, a detector (e.g. photodetector) utilized in the prior art is relatively insensitive to beams of radiation when supplied thereto by an associated emitter that is located several (i.e. seven or more) feet away. As a result, the prior art optical systems would be highly unreliable for detecting unauthorized patient movements, if employed in combination with a hospital bed, or the like.

SUMMARY OF THE INVENTION

Briefly, and in general terms, a patient activity monitoring system is disclosed which provides both visual and audible, local and remote alarms to supervisory personnel in the event that a patient, who is otherwise confined to his bed, attempts any unauthorized movement or departure therefrom. The monitoring system, in a preferred embodiment thereof, includes an array of infrared radiation emitters and phototransistor detectors aligned with one another between the footboard and the headboard of the bed. By virtue of a unique biasing circuit, the phototransistors are highly sensitive to beams of infrared radiation that are transmitted by the emitters from distances of approximately seven feet. Pulsed output signals from each of the phototransistors are applied to the inputs of respective first signal processors. The first signal processors operate as resonant amplifiers to, thereby, amplify and shape the pulsed output signals and eliminate ambient and noise signals. The outputs of the first signal processors are supplied to the inputs of second signal processors. The second signal processors include respective timing means which operate to count missing pulses in the event that a patient's unauthorized or excessive movements interrupt the transmission of infrared energy between the array of emitters and detectors. When the time to count the missing pulses exceeds a predetermined time delay to account for random or inadvertent patient movement, either of the second signal processors may generate warning signals that are indicative of the unauthorized or excessive patient movements. The warning signals are applied to an encoder which supplies coded warning signal messages to each of a pair of bedside transmitters via a local and a remote channel. The transmitters broadcast the coded messages to respective local and remote receivers, whereby the messages are decoded to subsequently alert supervisory personnel to unauthorized patient movement and the possibility of impending patient injury.

DESCRIPTION OF THE PREFERRED EMBODIMENT

Figure 1:
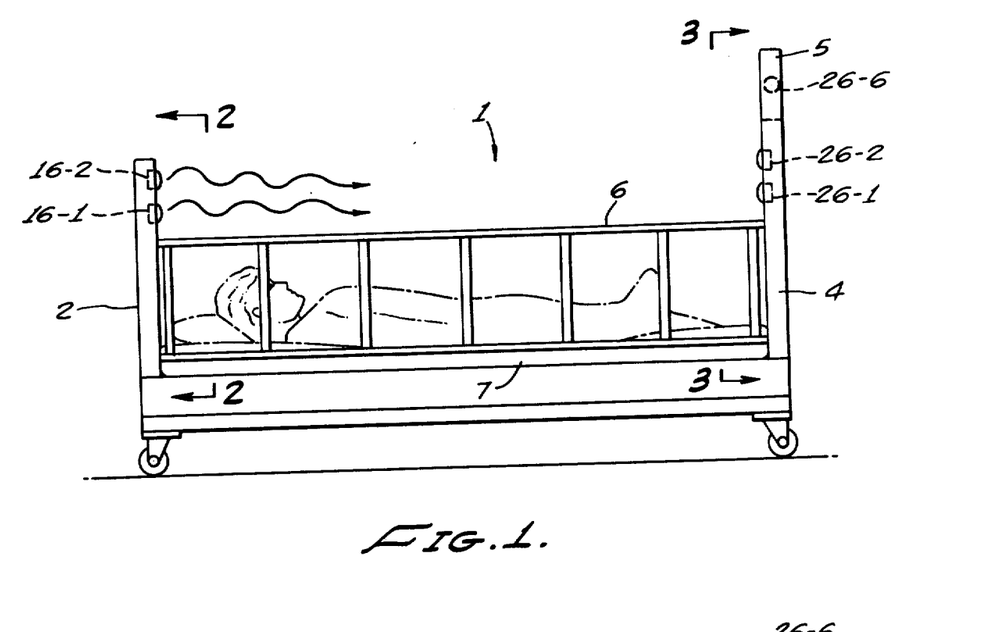
FIG. 1 of the drawings illustrates an array of radiant energy emitters and photodetectors of the presently disclosed patient activity monitoring system arranged in the headboard and footboard of a patient's bed.
Figure 2:
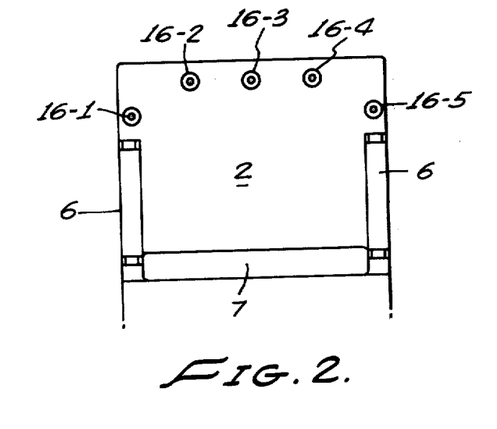
FIG. 2 shows a view of the headboard of the patient's bed taken along lines 2—2 of FIG. 1.
Figure 3:
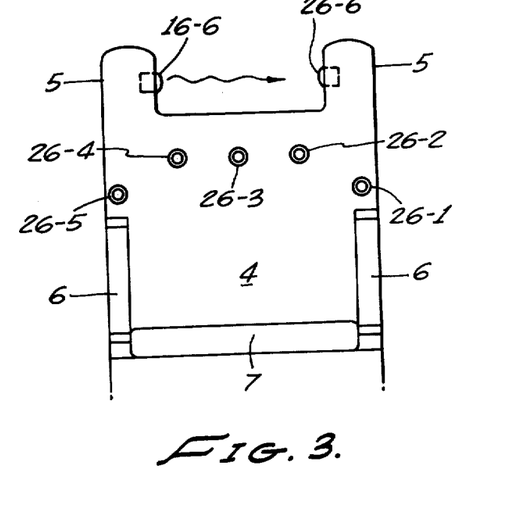
FIG. 3 shows a view of the footboard of the patient's bed taken along lines 3—3 of FIG. 1.

Referring concurrently to FIGS. 1, 2 and 3 of the drawings, a patient's bed 1 is illustrated to be used in conjunction with the patient activity monitoring system that forms the present invention. The bed 1 is conventional, having a headboard 2, a footboard 4, and a pair of movable side rails or panels 6 and a mattress 7. The side panels 6 help to constrain an overactive patient and, thereby, prevent him from falling over the sides of the bed. However, the footboard 4 of the bed 1 may be modified to include a raised extension 5 at each end thereof. In order to monitor the movements of a patient who is confined to the bed 1 and to alert supervisory personnel in the event that the patient attempts an unauthorized departure therefrom, an array of radiant energy emitters and a corresponding array of radiant energy detectors are installed in the headboard 2 and footboard 4 of the bed 1.

More particularly, and in accordance with the present invention, the array of radiant energy emitters comprises six devices 16-1, 16-2, 16-3, 16-4, 16-5 and 16-6. An emitter source of supply of invisible radiant energy, such as infrared light, or the like, is preferred in order to prevent undesirable inconveniences or disturbances to the patient during, for example, the evening hours. As best illustrated in FIG. 2, five infrared emitters 16-1 . . . 16-5 are attached at locations within the headboard 2. Emitters 16-1 and 16-5 are respectively positioned over each one of the bed side panels 6. Three equally spaced emitters 16-2, 16-3 and 16-4 are positioned above the mattress 7 so as to divide the bed 1 into (e.g. four) detection zones for accurately monitoring any unauthorized or excessive movements of the patient. The sixth infrared emitter 16-6 is attached at a location within one of the raised extensions 5 of the footboard 4.

The array of radiant energy detectors comprises six photosensitive devices 26-1, 26-2, 26-3, 26-4, 26-5 and 26-6, such as phototransistors, or the like. As best illustrated in FIG. 3, each of the six photodetectors 26-1 . . . 26-6 is attached to the footboard 4 of the bed 1 in substantial alignment with a corresponding one of the emitters 16-1 . . . 16-6 in order to receive a supply of infrared radiation emanating therefrom. That is, detectors 26-1 and 26-5 are respectively positioned over each one of the bed side panels 6 and opposite the corresponding locations of the emitters 16-1 and 16-5. Three detectors 26-2, 26-3 and 26-4 are positioned above the mattress 7 of the bed 1 and opposite the corresponding locations of the emitters 16-2, 16-3 and 16-4. The sixth detector 26-6 is attached at a location within the second of the raised extensions 5 of the footboard 4 and opposite the corresponding location of the emitter 16-6. The specific number and location of the emitters and corresponding detectors are chosen in order to conveniently and accurately detect any unauthorized or excessive movements of a patient in his bed. However, it is within the scope of this invention to utilize any other numbers of emitters and detectors at various suitable positions to accomplish the purpose of this invention.

The presently disclosed patient activity monitoring system is capable of two modes of operation. In a first, perimeter mode of operation, each of the infrared emitters 16-1, 16-5 and 16-6 as well as the corresponding photodetectors 26-1, 26-5 and 26-6 are selectively energized. The remaining detectors are inactivated during the first mode of operation. Therefore, in the perimeter mode, beams of invisible infrared energy are transmitted between emitter and detector pairs over each of the bed side panels 6 and across the bed footboard 4 (between the raised extensions 5 thereof). Hence, in the perimeter mode of operation, a patient is given the freedom to sit up or to change his position (i.e. roll over) in the bed 1. However, should he, without authorization, attempt to seek an egress from the bed, over either of the side panels 6 or the footboard 4, the respective beam of infrared energy emanating from one of the emitters 16-1, 16-5 or 16-6 is interrupted. As will be explained in greater detail hereinafter, whenever the transmission of an infrared beam between an emitter-detector pair (e.g. 16-1 and 26-1, 16-5 and 26-5 or 16-6 and 26-6) is interrupted during the perimeter mode for a first predetermined length of time, both audio and visual alarms may be activated to immediately alert supervisory personnel to the patient's unauthorized efforts to depart from his bed.

In a second, blanket mode of operation, all of the emitter-detector pairs of the patient activity monitoring system are concurrently energized. The blanket mode is desirable when a patient must remain completely immobile. Therefore, during the blanket mode, beams of invisible infrared energy are also transmitted between emitter-detector pairs (e.g. 16-2 and 26-2, 16-3 and 26-3, and 16-4 and 26-4) over the top surface of the mattress 7 of the bed 1. Hence, in the blanket mode of operation, should the patient attempt to either sit up or depart from the bed 1 without authorization, one or more respective beams of infrared energy emanating from the emitters 16-1 . . . 16-6 are interrupted. As will also be explained in greater detail hereinafter, whenever the transmission of an infrared beam between an emitter-detector pair is interrupted during the blanket mode for a second predetermined length of time, both audio and visual alarms may be activated, as disclosed above.

Figure 4:
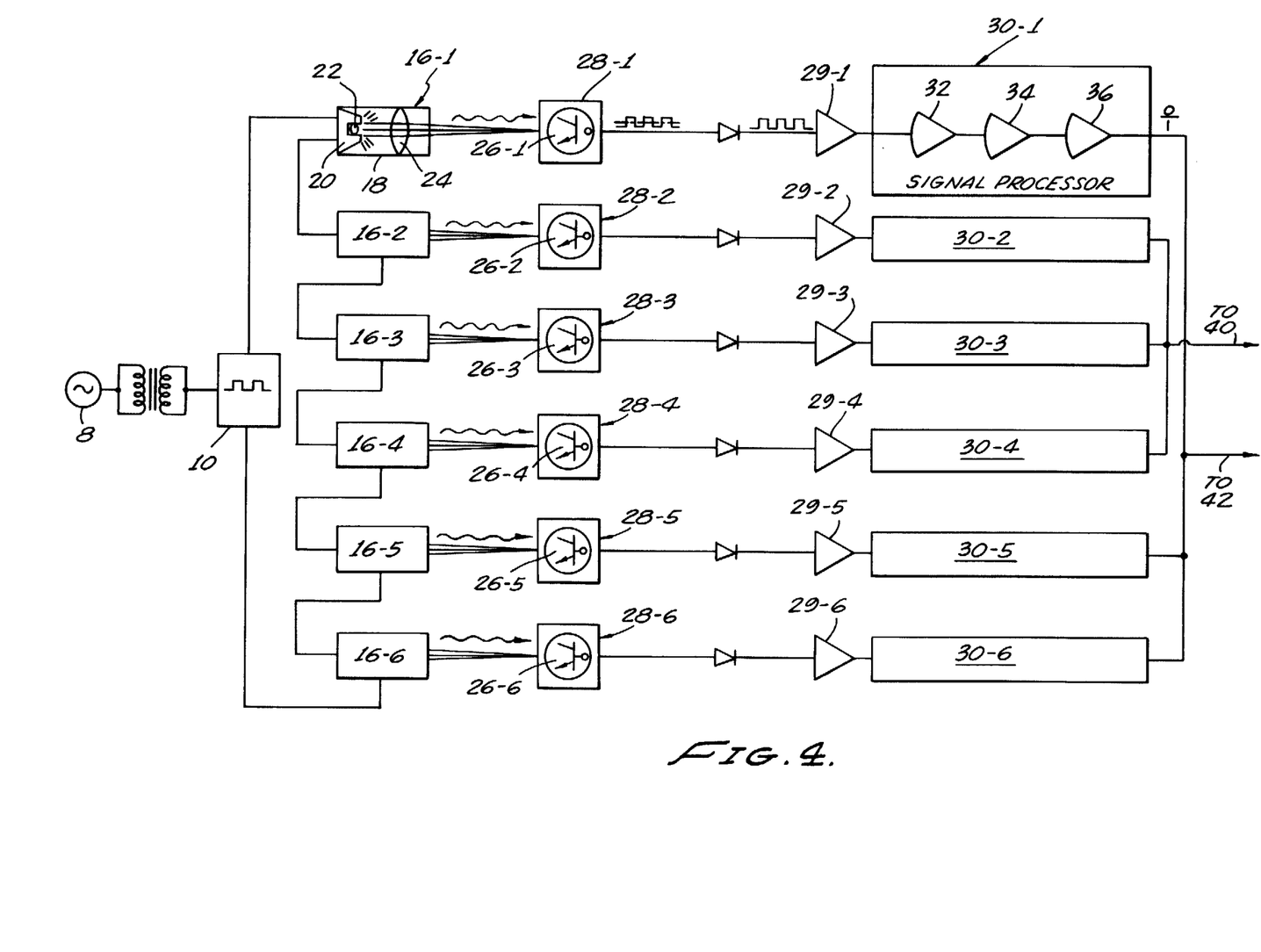
FIGS. 4 and 5 comprise of a block diagram representing the electronics utilized to implement the presently disclosed patient activity monitoring system.
Figures 5, 6A, 6B:
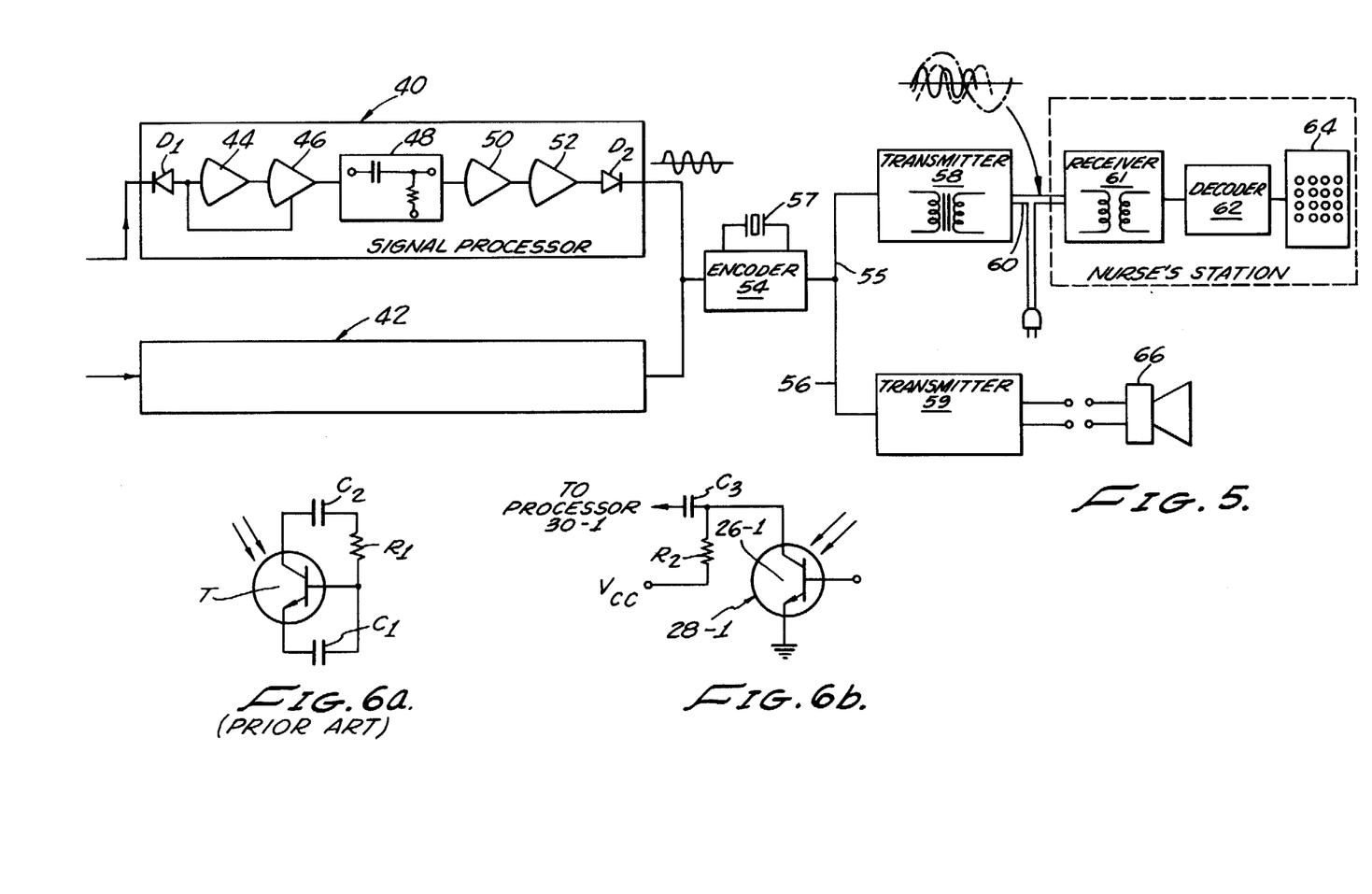
FIG. 6a shows a prior art circuit for biasing a phototransistor detector.
FIG. 6b shows a unique circuit for biasing a phototransistor detector to enable said phototransistor to be highly sensitive to radiant energy that is transmitted thereto from distances of approximately seven feet or more.

Referring concurrently to FIGS. 4 and 5 of the drawings, a block diagram is shown wich is representative of the circuitry utilized to implement the presently disclosed patient activity monitoring system. The source of infrared energy comprises an array of six identical emitters 16-1, 16-2, 16-3, 16-4, 16-5 and 16-6 that are connected in electrical series with one another. As previously disclosed while referring to FIGS. 1-3, five of the emitters 16-1 . . . 16-5 are positioned in the headboard of the patient's bed while the sixth emitter 16-6 is located in a first extension of the bed footboard. Each emitter (for example, 16-1) includes a plastic tube 18, or the like, which encloses a dimpled header 20. The dimpled header 20 contains the infrared active element 22. In a preferred embodiment of the invention, the active element 22 is gallium arsenide which emits low power, invisible infrared radiation at a wavelength in the range of 900-940 nanometers. The infrared radiation is collimated by a suitable lensing arrangement 24, so that a spot of infrared radiation having a diameter of approximately seven inches is received by a detector, which detector is typically located seven feet therefrom and in the footboard of the bed.

Each of the emitters 16-1 . . . 16-6 is pulsed by a conventional D.C. pulser 10, whereby pulsed infrared radiation is emitted at a frequency of about 1 kHz. The pulser 10 may be driven by either a suitable battery supply (not shown) or an isolated A.C. source 8. A 1 kHz pulse frequency of infrared emission is desirable for both convenience and to distinguish interfering noise and spurious ambient radiation signals.

The preferred infrared detector circuit comprises an array of six identical and conventional silicon phototransistor circuits 26-1, 26-2, 26-3, 26-4, 26-5 and 26-6. As disclosed when referring to FIGS. 1-3, five of the phototransistors 26-1 . . . 26-5 are positioned in the footboard of the patient's bed and in alignment with the five emitters 16-1 . . . 16-5. The sixth phototransitor 26-6 is positioned in a second extension of the footboard of the patient's bed and in alignment with the emitter 16-6.

Each of the phototransistor circuits is well known to those skilled in the art. However, and in accordance with another preferred embodiment of the present invention, the sensitivity of the phototransistor circuits is maximized so as to be highly responsive to the infrared radiation transmitted by the emitters 16-1 . . . 16-6 over relatively long distances (e.g. seven feet or more between the headboard and footboard of the bed). This is accomplished by means of phototransistor biasing circuits 28-1 . . . 28-6. FIG. 6a shows the conventional circuit technique for biasing a phototransistor T. As illustrated in the prior art technique, one plate of a capacitor $C_1$ is connected to the emitter electrode of the phototransistor T. The base electrode of the phototransistor T is connected at an electrical junction with the second plate of the capacitor $C_1$ and one terminal of a resistor $R_1$. The second terminal of the resistor $R_1$ is connected to one plate of a capacitor $C_2$. The second plate of capacitor $C_2$ is connected to the collector electrode of the phototransistor T. As a consequence of the prior art biasing technique, a phototransistor has heretofore been relatively insensitive to radiant energy which is transmitted from several feet away. That is, a phototransistor has heretofore been undesirably susceptible to the presence of ambient light signals. Moreover, the phototransistor operates primarily in the dark current region.

FIG. 6b illustrates an improved biasing circuit (e.g. 28-1) which renders a respective detector phototransistor (e.g. 26-1) highly sensitive to infrared energy that is transmitted from distances of seven to twelve feet or more. The emitter electrode of the phototransistor 26-1 is connected to a first source of reference potential, such as ground. The collector electrode of the phototransistor 26-1 is connected at an electrical junction with one plate of a capacitor $C_3$ and one terminal of a resistor $R_2$. The second terminal of the resistor $R_2$ is connected to a second source of reference potential, $V_{CC}$. The second plate of the capacitor $C_3$ is connected to the input terminal of a signal processor via a sampling diode and an an amplification stage (as shown in FIG. 4). The base electrode of the phototransistor 26-1 is open circuited. By virtue of the improved biasing circuit 28-1, the dynamic operating range of the open base phototransistor 26-1 is increased. Moreover, the entire base-to-collector current amplification parameter $(\beta)$ of the phototransistor is shifted, whereby the operating point of the phototransistor 26-1 is rapidly adjusted to the quiescent operating point.

As long as the supply of infrared radiation remains uninterrupted, each of the phototransistors 26-1 . . . 26-6 continuously applies output pulses at a frequency of 1 kHz to the input terminals of six signal processors 30-1, 30-2, 30-3, 30-4, 30-5 and 30-6 via a respective input sampling diode and a respective series connected high gain amplifier stage 29-1, 29-2, 29-3, 29-4, 29-5 and 29-6. Since the circuitry of each signal processor 30-1 . . . 30-6 is identical, only signal processor 30-1 is described in detail. The signal processor 30-1 comprises three series connected operational amplifier stages 32, 34 and 36. The operational amplifiers 32, 34 and 36 are interconnected (with suitable passive components) so as to condition or shape the pulsed 1 kHz signal and to eliminate or discriminate against any spurious pulses (such as, for example, ambient light signals) having frequencies other than 1 kHz. Moreover, any noise signals occurring at the open base electrode of the phototransistor detectors 26-1 . . . 26-6 are blocked. Therefore, in operation, the respective operational amplifiers 32, 34 and 36 of each of the signal processors 30-1 . . . 30-6 functions as a conventional resonant amplifier, such as a well known LM 3900N microelectronic chip utilized thereas.

As illustrated in FIGS. 4 and 5, the amplified 1 kHz output pulses from each of the three signal processors 30-2, 30-3 and 30-4 are supplied to the input terminals of a first additional signal processor 40 via an input channeling diode $D_1$. Therefore, the first additional signal processor 40 is responsive to any pulse signals that may be supplied thereto from the output of the respective phototransistor detector circuits 26-2, 26-3 and 26-4. As earlier disclosed, the phototransistors 26-2, 26-3 and 26-4 are activated only during the blanket mode of operation in order to detect a monitored patient who, without authorization, sits up, raises an appendage, etc. The amplified 1 kHz output pulses from each of the three signal processors 30-1, 30-5 and 30-6 are supplied to the input terminal of a second additional signal processor 42 via an input channeling diode (not shown). Therefore, the second additional signal processor 42 is responsive to any pulse signals that may be supplied thereto from the output of the respective phototransistor detectors 28-1, 28-5, and 28-6. As also earlier disclosed, the phototransistors 28-1, 28-5 and 28-6 are activated in both the blanket and perimeter modes of operation in order to detect a monitored patient who either grabs the side rail of his bed or attempts to depart therefrom without authorization.

Each of the first and second additional signal processors 40 and 42 are implemented as substantially identical missing pulse counters, such as a well known LM 358 microelectronic chip utilized thereas. Therefore, only the first additional signal processor 40 is disclosed in detail. More particularly, the first additional signal processor 40 comprises a pair of series connected operational amplifiers 44 and 46 connected to receive the output pulse signals from the input channeling diode $D_1$. An output terminal of the amplifier 46 is fed back to an input terminal of the amplifier 44, whereas the combination of operational amplifiers 44 and 46 operates as a feedback amplifier to substantially eliminate any remaining undesirable spurious signals. The output pulse signals of the amplifier 46 are supplied to the input terminal of a timer 48. By way of example, the timer 48 is a well known LM (Linear Module) 555 microelectronic chip which, in a preferred application, is sensitive to the absence of amplified pulse signals that are otherwise supplied thereto from each of the signal processors 30-2, 30-3, and 30-4.

In operation, whenever the patient activity monitoring system is selectively switched into the blanket mode of operation and a patient assumes any unauthorized position in his bed that interrupts the transmission of infrared energy between any of the emitter-detector pairs 16-2 and 26-2, 16-3 and 26-3, or 16-4 and 26-4, the timer 48 accordingly responds by counting consecutive missing pulses blocked therefrom. To distinguish inadvertent and accidental motion from intentional and unauthorized movements of the patient, the timer 48 provides the instant monitoring system with a first predetermined time delay. The timer 48 includes a conventional R-C circuit, whereby the time constant thereof may be selectively adjusted to correspond to any suitable time delay. Typically, a relatively long time delay of approximately 2.5 seconds is desirable for timer 48 in order to account for random and inadvertent movements by a restless patient without unnecessarily alerting supervisory personnel. Should the number of consecutive absent pulses counted by the timer 48 exceed the predetermined first time delay, an output warning signal is generated from the timer 48 to a pair of series connected operational amplifiers 50 and 52. The warning signal is thereby amplified for subsequent application from an output terminal of the first additional signal processor 40 to an input terminal of an encoder 54 via an output channeling diode $D_2$. However, in the event that the transmission of infrared energy is not interrupted for a period of time in excess of the first time delay, no output signal is generated by the signal processor 40 in the blanket mode of operation.

Whenever the patient activity monitoring system is selectively switched into either of the perimeter or blanket modes of operation and a patient attempts an unauthorized departure from his bed so as to interrupt the transmission of infrared energy between any of the emitter-detector pairs 16-1 and 26-1, 16-5 and 26-5, or 16-1 and 26-6, a timer or missing pulse counter (not shown) associated with the second additional signal processor 42 immediately responds by counting consecutive absent pulses. To distinguish accidental from intentional movements of the patient, the time associated with the signal processor 42 provides the present monitoring system with a second predetermined time delay by means of an R-C circuit (also not shown). The first and second additional signal processors 40 and 42 differ from one another by the selection of their respective timer R-C time constants. That is, a relatively short time delay of approximately 0.1 seconds or less is typically desired for the last mentioned timer of the signal processor 42, inasmuch as once an overactive patient who, without authorization, moves over the side rails or footboard of his bed, it may be essential that supervisory personnel be notified immediately to prevent the patient from incurring serious injury. Should the number of consecutive absent pulses counted by the timer of the signal processor 42 exceed the predetermined second time delay, a corresponding output warning signal is generated for subsequent amplification and application from an output terminal of the second additional signal processor 42 to an input terminal of the encoder 54. If the transmission of infrared energy is not interrupted for a period of time in excess of the second time delay, no output signal is generated by the signal processor 42 in either of the perimeter or blanket modes of operation.

The presently disclosed patient activity monitoring system is adapted to provide both locally and remotely stationed supervisory personnel with an indication of the unauthorized movements of a plurality (e.g. 16) of bed confined patients. Therefore, the encoder 54 provides output signals to first and second bedside transmitters 58 and 59 via a remote output channel 55 and a local output channel 56, respectively. In another preferred embodiment of the invention, the encoder 54 comprises the encoder portion of a conventional 2 of 8 DTMF (Dual Tone Multi-Frequency) encoder-decoder pair, such as a well known MK 5087N microelectronic chip utilized thereas. A suitable crystal 57 is connected to the encoder 54. The crystal 57 provides a supply of clock signals to the encoder 54, whereby the encoder generates a carrier signal (at 100 kHz) to energize the first bedside transmitter 58. Therefore, the encoder 54 of each bed provides a respective first bedside transmitter 58 with a signal that is a particular frequency coded message. Each particular message is frequency coded so as to distinguish the plurality of beds from one another in the event the generation of a warning signal is necessitated as the result of an unauthorized movement of several patients. The first transmitter 58 may comprise a resonant transformer such as a Toko YAN 60027N coil (that becomes resonant at 100 kHz), which transmits the frequency coded message by standard FM transmission on an AC carrier wave. As will be known by those skilled in the art, the first bedside transmitter 58 forms the first half of a conventional AC wire rider. A corresponding receiver 61, which receives the AC carrier wave from the bedside transmitter 58 via an AC power cord 60, forms the second half of the conventional AC wire rider. The receiver 61 may comprise a Toko YAN 60026N coil. The receiver 61 may be positioned at a nurse's aid station or any other suitable remote location.

The nurse's station may also include a well known decoder 62 and a remote alarm indicating means 64. The decoder 62 comprises the decoder portion of the conventional 2 of 8 DTMF encoder-decoder pair, such as a well known DTR 110 microelectronic circuit utilizing a Collins Radio CRC 8030 microelectronic decoder chip. The decoder 62 is connected to the output of the receiver 61 to decode the frequency coded message received thereby. By way of example, the remote indicating means 64 may be an array of lights arranged on a suitable console or the like, each light corresponding to one of the patients' beds. The decoder 62 supplies the required energization signal to actuate a particular light from the array thereof in response to a decoded warning signal, so as to thereby provide the nurse's station with a visual indication of the bed at which a potentially unsafe condition exits. It is to be understood, however, that the decoder may also activate an audio alarm at the nurse's station at the same time that the visual indication of impending patient injury is provided.

As previously disclosed, when a warning output signal is received from one of the additional signal processors 40 or 42, the encoder 54 supplies a corresponding signal to the second bedside transmitter 59 via the local output channel 56. The second bedside transmitter 59 is adapted to supply coded ultrasonic signals, or the like, to a local alarm 66 that may be positioned over or near the door of the patient's room. The local alarm 66 is responsive to the coded ultrasonic signals to provide an audible and visible indication of possible patient injury to any supervisory personnel that are passing outside the patient's room. One such coded ultrasonic transmitter-alarm receiver set that is suitable for utilization herein is a Gulton T 400 and R 400 ultrasonic transducer pair. Therefore, unlike the prior art monitoring systems, immediate attention may be provided to an overactive patient before he sustains serious injury as a consequence of unauthorized or excessive movements in or from his bed.

It will be apparent that while a preferred embodiment of the invention has been shown and described, various modifications and changes may be made without departing from the true spirit and scope of this invention. For example, although, in a preferred embodiment of the invention, infrared radiation techniques are utilized, any form of radiant energy, such as that in the electromagnetic or sound wave energy spectrum, may be substituted therefor. Hence, ultrasonic, ultraviolet or visible forms of radiation may also be used to monitor a patient for unauthorized movements in or from his bed.

Having thus set forth a preferred embodiment of the present invention, what is claimed is:

1. A system to monitor the movements and activity of a bed confined patient and to provide an indication of unauthorized patient movement, said system including:
   a plurality of radiant energy emitters positioned at the bed of the patient to be monitored,
   a corresponding plurality of radiant energy sensitive detector circuits positioned at the bed of the patient and in spaced alignment with said emitters, said detector circuits generating output signals having a particular frequency in response to a supply of radiant energy received from said emitters,
   a plurality of first signal processing means respectively connected to receive and amplify the output signals of each of said detector circuits,
   at least a first and a second additional signal processing means, said first additional signal processing means connected to receive output signals from some of said plurality of first signal processing means, and said second additional signal procesing means connected to receive output signals from some other of said plurality of first signal processing means,
   each of said first and second additional signal processing means having a respective timing means to provide corresponding first and second predetermined time delays to account for random or accidental patient movements, said first additional signal processing means adapted to generate a first output warning signal in the event that an unauthorized patient movement interrupts the supply of radiant energy between at least one of said emitters and corresponding radiant energy sensitive detector circuits for an interval of time in excess of said first predetermined time delay, and said second additional signal processing means adapted to generate a second output warning signal in the event that an unauthorized patient movement interrupts the supply of radiant energy between at least a second of said emitters and corresponding radiant energy sensitive detector circuits for an interval of time in excess of said second predetermined time delay, and
   alarm means connected to receive the first and second output warning signals generated by said first and second additional signal processing means so as to thereby provide an indication of unauthorized patient movements.

2. The patient activity monitoring system recited in claim 1, wherein said radiant energy emitters emit infrared light energy that is invisible to the naked human eye.

3. The patient activity monitoring system recited in claim 2, wherein each of said radiant energy emitters includes an active element comprising galium arsenide to thereby emit the invisible infrared light energy.

4. The patient activity monitoring system recited in claim 1, wherein each of said plurality of radiant energy detector circuits includes a respective phototransistor, said respective phototransistor having an open circuited control electrode that is disconnected from any source of potential, whereby the sensitivity of said phototransistor to the supply of radiant energy emanating from said emitters is maximized.

5. The patient activity monitoring system recited in claim 1, wherein each of said first signal processing means comprises a resonant amplifier.

6. The patient activity monitoring system recited in claim 1, wherein each of said first and second additional signal processing means comprises a missing-pulse counter.

7. The patient activity monitoring system recited in claim 1, wherein the respective timing means of each of said first and second additional signal processing means comprises a missing pulse counter, each said missing pulse counter being activated to count for an interval of time during the absence of detector circuit output signals in the event that patient movement interrupts the supply of radiant energy between an emitter and a corresponding detector circuit, said first and second additional signal processing means generating the first and second warning signals, respectively, when the respective counts correspond to intervals of time that exceed said first and second predetermined time delays, respectively.

8. The patient activity monitoring system recited in claim 1, including encoder means connected between respective output terminals of said first and second additional signal processing means and said alarm means,
   said encoder means responsive to either of the first or second output warning signals generated by said first and second additional signal processing means in order to provide a particular frequency coded message that is indicative of a designated bed at which an unauthorized movement of a patient occurs.

9. The patient activity monitoring system recited in claim 8, further including transmitter means connected between said encoder means and said alarm means in order to transmit said frequency coded message to said alarm means.

10. The patient activity monitoring system recited in claim 9, wherein said transmitter means is adapted to transmit ultrasonic signals to said alarm means.

11. The patient activity monitoring system recited in claim 9, wherein said transmitter means comprises a resonant transformer.

12. The patient activity monitoring system recited in claim 11, further including receiver means connected between said transmitter means and said alarm means,
   said receiver means connected to said transmitter means resonant transformer by means of an A.C. power cord, whereby said receiver means receives the frequency coded message from said transmitter means over the A.C. power cord.

13. The patient activity monitoring system recited in claim 12, further including decoder means connected between said receiver means and said alarm means to decode the frequency coded message provided by said encoder means, whereby said alarm means is supplied with a signal that is indicative of the designated bed at which an unauthorized movement of a patient occurs,
   said encoder means and said decoder means comprising a Dual Tone Multi-Frequency pair.

14. A patient activity monitoring system having at least two modes of operation, said monitoring system including:

a first plurality of radiant energy supplying emitters and a corresponding first plurality of radiant energy sensitive detectors, said first pluralities of emitters and detectors arranged in spaced alignment with one another, said first pluralities of emitters and detectors activated during a first of said two modes of operation in order to detect certain unauthorized movements of a bed confined patient, a second plurality of radiant energy supplying emitters and a corresponding second plurality of radiant energy sensitive detectors, said second pluralities of emitters and detectors arranged in spaced alignment with one another, said second pluralities of emitters and detectors activated during a second of said two modes of operation in order to detect certain other unauthorized movements of a bed confined patient, said first and second pluralities of detectors generating output signals in response to radiant energy supplied thereto by said corresponding first and second pluralities of emitters, a plurality of means, each being connected to receive and amplify the output signal generated by a corresponding one of said first and second pluralities of detectors and to substantially block the transmission of spurious signals, first and second signal processing means respectively responsive to the absence of an output signal generated by one of said first and second pluralities of detectors and received from said amplification and signal blocking means, said first signal processing means activated to generate a first output warning signal after a first predetermined time delay and during the first mode of operation in the event that the certain unauthorized patient movement interrupts the supply of radiant energy between at least one emitter and detector of said first pluralities of emitters and detectors, said second signal processing means activated to generate a second output warning signal after a second predetermined time delay and during the second mode of operation in the event that the certain other unauthorized patient movement interrupts the supply of radiant energy between at least one emitter and detector of said second pluralities of emitters and detectors, and alarm means responsive to the first or second output warning signal generated by said first or second signal processing means in each of the first and second modes of operation to provide an indication of unauthorized patient movement.

15. The patient activity monitoring system recited in claim 14, wherein the bed of the patient to be monitored has a headboard and a footboard, some of said first and second pluralities of radiant energy supplying emitters being located in the bed headboard, and some of said corresponding first and second pluralities of radiant energy sensitive detectors being located in the bed footboard.

16. The patient activity monitoring system recited in claim 14, wherein each of said first and second pluralities of radiant energy sensitive detectors includes a phtotransistor having a pair of conduction path electrodes and a control electrode, a first of said conduction path electrodes connected to a source of supply voltage, the second of said conduction path electrodes connected to the corresponding detector signal amplification and noise blocking means, and said control electrode being open circuited.

17. The patient activity monitoring system recited in claim 14, wherein each of said first and second signal processing means includes respective first and second timing means, each of said respective timing means being adapted to count for an interval during the absence of detector output signals, said first signal processing means generating the first output warning signal when the count interval of said respective first timing means exceeds the first predetermined time delay, said second signal processing means generating the second output warning signal when the count interval of said respective second timing means exceeds the second predetermined time delay.

18. The patient activity monitoring system recited in claim 14, wherein each of said first and second pluralities of radiant energy emitters supplies infrared energy.

19. A patient activity monitoring system to detect unauthorized or excessive movements of a patient who is confined to a bed, said patient activity monitoring system comprising:

radiant energy emitter means to emit radiant energy across the patient's bed, radiant energy detector means aligned with said emitter means at a location across the patient's bed so as to receive the radiant energy generated by said emitter means, and alarm means operative to produce an alarm signal when receipt of radiation by said detector means is interrupted by a patient moving into a position between said emitter means and said detector means, said emitter means and said detector means being aligned so that radiant energy therebetween is not blocked in the normal patient position in the bed and is blocked when the patient assumes any unauthorized position in the bed.

20. The patient activity monitoring system recited in claim 19, wherein said system is adapted to operate in at least two modes of operation, at least some of said radiant energy emitter and detector means energized in a first mode of operation to detect certain unauthorized or excessive movements of the bed confined patient, and at least some other of said radiant energy emitter and detector means energized in the second mode of operation to detect certain other unauthorized or excessive movements of the bed confined patient.

21. the patient monitoring system recited in claim 19, wherein said emitter means emits radiant energy in the infrared spectrum.

22. The patient monitoring system recited in claim 19, wherein said emitter means emits radiant energy in the elecromagnetic spectrum.

23. The patient monitoring system recited in claim 19, wherein said emitter means emits radiant energy in the ultraviolet spectrum.

24. The patient monitoring system recited in claim 19, wherein said emitter means emits radiant energy in the visible light spectrum.

25. The patient monitoring system recited in claim 19, wherein said emitter means emits radiant energy in the ultrasonic spectrum.

26. The patient monitoring system recited in claim 19, wherein said alarm means is located at a remote position from said patient's bed.

27. The patient monitoring system recited in claim 19, further including:
   encoder means to provide a coded warning signal that is indicative of the interruption of the receipt of radiation by said detector means,
   transmitter means to transmit the coded warning signal,
   receiver means to receive the transmitted coded warning signal, and
   decoder means to decode the coded warning signal for application to said alarm means, said alarm means being responsive to said decoded warning signal to thereby produce said alarm signal.

28. A method of monitoring unauthorized or excessive movements of a patient on a bed, said method including the steps of:
   transmitting energy across the bed to locations such that the energy is not blocked in normal patient positions on said bed and is blocked when the patient assumes an unauthorized position in the bed,
   detecting the blockage of the energy being transmitted, and
   activating an alarm upon detecting such blockage.

* * * * *